United States Patent
Shen (10) Patent No.: US 12,420,106 B2
(45) Date of Patent: Sep. 23, 2025

(54) POWER CIRCUIT AND AUTOMATED EXTERNAL DEFIBRILLATOR COMPRISING THE SAME

(71) Applicant: Infineon Technologies Austria AG, Villach (AT)

(72) Inventor: Song Shen, Shenzhen (CN)

(73) Assignee: INFINEON TECHNOLOGIES AUSTRIA AG, Villach (AT)

( * ) Notice: Subject to any disclaimer, the term of this patent is extended or adjusted under 35 U.S.C. 154(b) by 585 days.

(21) Appl. No.: 17/871,191

(22) Filed: Jul. 22, 2022

(65) Prior Publication Data

US 2023/0022000 A1    Jan. 26, 2023

(30) Foreign Application Priority Data

Jul. 23, 2021    (CN) .......................... 202121695040.4

(51) Int. Cl.
| | |
|---|---|
| *A61N 1/39* | (2006.01) |
| *H02J 7/00* | (2006.01) |
| *H02J 7/34* | (2006.01) |
| *H02M 3/335* | (2006.01) |

(52) U.S. Cl.
CPC ......... *A61N 1/3981* (2013.01); *A61N 1/3904* (2017.08); *H02J 7/0068* (2013.01); *H02J 7/345* (2013.01); *H02M 3/33592* (2013.01)

(58) Field of Classification Search
CPC .. A61N 1/3975; A61N 1/3904; A61N 1/3981; A61N 1/3925; A61N 1/378; A61N 1/3912; A61N 1/3968; A61N 1/3918; A61N 1/3625; A61N 1/3993; A61N 1/0563; A61N 1/37; A61N 1/395; A61N 1/3906; H02J 2310/23; H02J 7/0063; H02J 7/0068
See application file for complete search history.

(56) References Cited

U.S. PATENT DOCUMENTS 7,050,850 B2 *    5/2006    Norton ................. A61N 1/3975
607/5

* cited by examiner

*Primary Examiner* — Deborah L Malamud
(74) *Attorney, Agent, or Firm* — Cooper Legal Group LLC (57) ABSTRACT

Disclosed are a power circuit and an automated external defibrillator including the same. The power circuit may include a battery-driven power source, and a transformer comprising a primary winding and N secondary windings, wherein N is an integer greater than or equal to 2, and wherein the primary winding is electrically coupled to the power source. The power circuit may include N charging and discharging branches, wherein the N charging and discharging branches are respectively connected to the N secondary windings and are cascaded in sequence. The power circuit may include a plurality of electrode plates configured to be connected to an external load, wherein electrode plates of the plurality of electrode plates are electrically coupled to one or more output nodes of the N charging and discharging branches.

20 Claims, 9 Drawing Sheets

POWER CIRCUIT AND AUTOMATED EXTERNAL DEFIBRILLATOR COMPRISING THE SAME

RELATED APPLICATION

This application claims priority to Chinese Patent Application No. 202121695040.4, filed on Jul. 23, 2021, entitled "POWER CIRCUIT AND AUTOMATED EXTERNAL DEFIBRILLATOR COMPRISING THE SAME", which is incorporated by reference herein in its entirety.

TECHNICAL FIELD

The present disclosure relates generally to power electronics, for example to a power circuit for an automated external defibrillator (AED).

BACKGROUND

An automated external defibrillator (AED) is a portable electronic device that automatically diagnoses the life-threatening cardiac arrhythmias of ventricular fibrillation (VF) and pulseless ventricular tachycardia in a patient, and is able to treat them through defibrillation. It applies electrical therapy which stops the arrhythmia, allowing the heart to reestablish an effective rhythm. Existing power circuits for AEDs may have short supply cycles and long delivery cycles, and may be expensive.

SUMMARY

The present disclosure will be summarized below to provide a basic understanding of certain aspects of the present disclosure. It should be understood that the summary is by no means an exhaustive summary of the present disclosure. It is not intended to identify key or essential parts of the present disclosure or to limit the scope of the present disclosure. Its sole purpose is to explain some concepts in a simplified form as an introduction to a more detailed description provided later.

In view of the above-described problems, an objective of the present disclosure is to provide a power circuit for an automated external defibrillator (AED) that can address one or more of the shortcomings of some power circuits.

According to an aspect of the present disclosure, a power circuit for an AED is provided, comprising: a power source (e.g., a battery-driven power source); a transformer comprising a primary winding (e.g., one primary winding) and N secondary windings, wherein N is an integer greater than or equal to 2, and wherein the primary winding is electrically coupled to the power source; N charging and discharging branches, wherein the N charging and discharging branches are respectively connected to N secondary windings and are cascaded in sequence; and a plurality of electrode plates configured to be connected to an external load, wherein electrode plates of the plurality of electrode plates are electrically coupled to one or more output nodes of the N charging and discharging branches (e.g., the electrode plates of the plurality of electrode plates are electrically coupled to one of the output nodes of the N cascaded charging and discharging branches, respectively).

In some examples, a charging and discharging branch of the N charging and discharging branches comprises a charging branch and a discharging branch, wherein N discharging branches of the N charging and discharging branches are cascaded with each other. In an example, the N charging and discharging branches comprise N pairs of charging branches and discharging branches, wherein the N discharging branches in the N pairs of charging branches and discharging branches are cascaded with each other.

In some examples, a charging branch of the N charging and discharging branches comprises a capacitor that is charged through the charging branch during charging to increase a voltage output to a discharging branch.

In some examples, the charging branch comprises a first diode, an inductor, and a second diode, wherein the second diode is connected across the inductor, and wherein the first diode, the inductor, and the capacitor are connected in series.

In some examples, an anode of the first diode is connected to a first end of a secondary winding, wherein a cathode of the first diode is connected to a first end of the inductor, wherein an anode of the second diode is connected to the cathode of the first diode, wherein a cathode of the second diode is connected to a second end of the inductor, wherein a first end of the capacitor is connected to the second end of the inductor, and wherein a second end of the capacitor is connected to a second end of the secondary winding.

In some examples, the discharging branch comprises a full-bridge circuit electrically coupled across the capacitor.

In some examples, the plurality of electrode plates are connected between an output node of the full-bridge circuit and an output node of a second full-bridge circuit of a second discharging branch of the N discharging branches.

In some examples, the full-bridge circuit comprises a first output node and a second output node, wherein a second full-bridge circuit, of a second discharging branch of the N discharging branches, comprises a third output node and a fourth output node, wherein the first output node of the full-bridge circuit is connected to the third output node of the second full-bridge circuit, wherein the fourth output node of the second full-bridge circuit is connected to an output node of a third full-bridge circuit of a third discharging branch of the N discharging branches, and wherein the external load is electrically coupled between the second output node of the full-bridge circuit and a fifth output node of a fourth full-bridge circuit of a fourth discharging branch of the N discharging branches.

In some examples, the fourth full-bridge circuit comprises a sixth output node, wherein the plurality of electrode plates are connected between an output node, of the first output node and the second output node, of the full-bridge circuit, and an output node, of the fifth output node and the sixth output node, of the fourth full-bridge circuit.

In some examples, the full-bridge circuit comprises a first transistor, a second transistor, a third transistor, and a fourth transistor, wherein the first output node of the full-bridge circuit is a node located on a bridge arm comprising the first transistor and the second transistor, and the second output node of the full-bridge circuit is a node located on a bridge arm comprising the third transistor and the fourth transistor.

In some examples, respective drive signals for N full-bridge circuits of the N discharging branches are synchronous.

In some examples, respective drive signals for N full-bridge circuits of the N discharging branches are asynchronous.

In some examples, a number of turns of a secondary winding of the N secondary windings is a function of N (such as where the number of turns decreases as N increases).

According to an aspect of the present disclosure, an automated external defibrillator is provided, comprising the power circuit according to the above-mentioned aspect of the present disclosure.

Other aspects of embodiments of the present disclosure will be provided in the following description, wherein preferred embodiments for fully disclosing embodiments of the present disclosure will be described in detail, without imposing any limitations thereon.

BRIEF DESCRIPTION OF THE DRAWINGS

The present disclosure may be better understood by reference to the detailed description given below in conjunction with the drawings, wherein the same or similar reference signs are used throughout the drawings to denote the same or similar components. The drawings, which are incorporated in this description together with the following detailed explanations and constitute a part of the description, serve to further illustrate preferred embodiments of the present disclosure and to explain the principles and advantages of the present disclosure. Among the drawings.

DETAILED DESCRIPTION

Exemplary embodiments of the present disclosure will be described below with reference to the drawings. For the sake of clarity and conciseness, not all features of an actual embodiment are detailed in the description. It should be understood, however, that many embodiment-specific decisions may be made in the development of any such actual embodiment in order to achieve a developer's specific goal, and that these decisions may vary with embodiments.

It should also be noted that, in order to prevent unnecessary details from obscuring the present disclosure, only components closely related to a solution according to the present disclosure are shown in the drawings, while other details that bear little relevance to the present disclosure are omitted.

in addition, terms such as first, second, A, B, (a), and (b) may be used herein to describe components of the present disclosure. Such terms are only used to differentiate one component from other components, and the properties, order, sequence, etc. of the corresponding components are not limited by the corresponding terms. Where a component is described as being "connected to" or "coupled to" another component, it should be construed that the component may be directly "connected to" or "coupled to" another component, or may be "connected to" or "coupled to" another component via an intermediate component.

Figure 1:
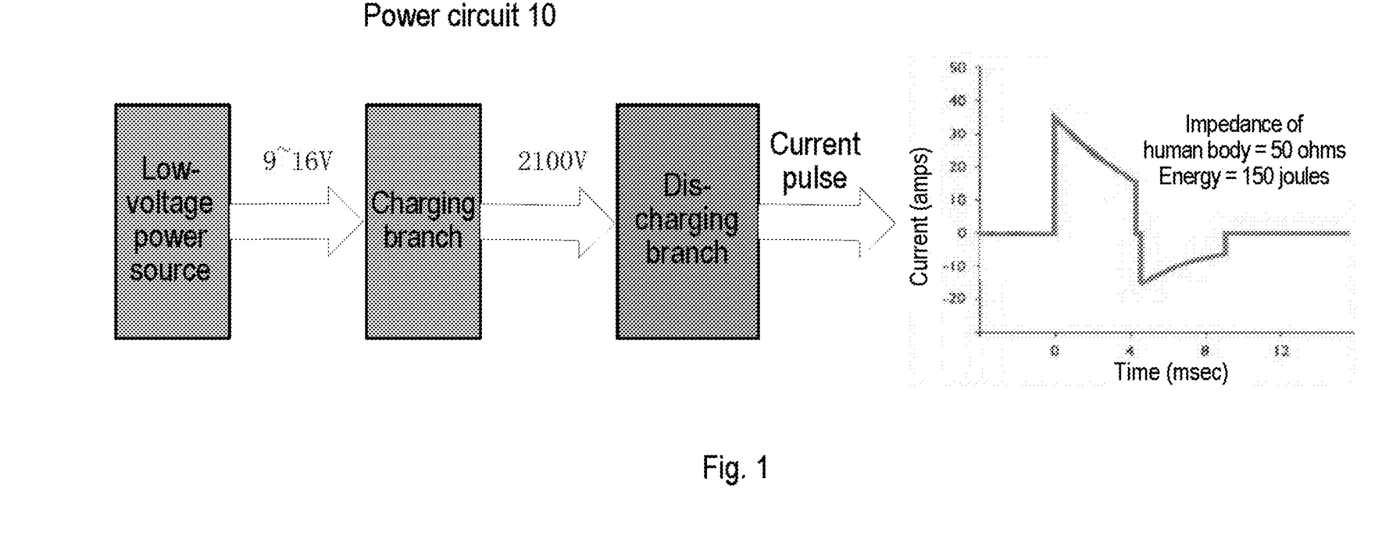
FIG. 1 is a schematic block diagram of an existing power circuit for an automated external defibrillator (AED) and a current waveform output by the power circuit.

FIG. 1 is a schematic block diagram of a power circuit 10 for an automated external defibrillator (AED). As shown in FIG. 1, the power circuit 10 comprises a low-voltage power source, a charging branch, and a discharging branch. The power circuit 10 converts a low voltage of 9 volts (V)-16 V of a low-voltage power source, for example, a battery, into a high voltage of 2100 V through the charging branch, and then the discharging branch releases a current pulse according to the impedance of a human body. Generally, the impedance offered by a human body is 50 ohms, corresponding to 150 joules of energy.

Figure 2A:
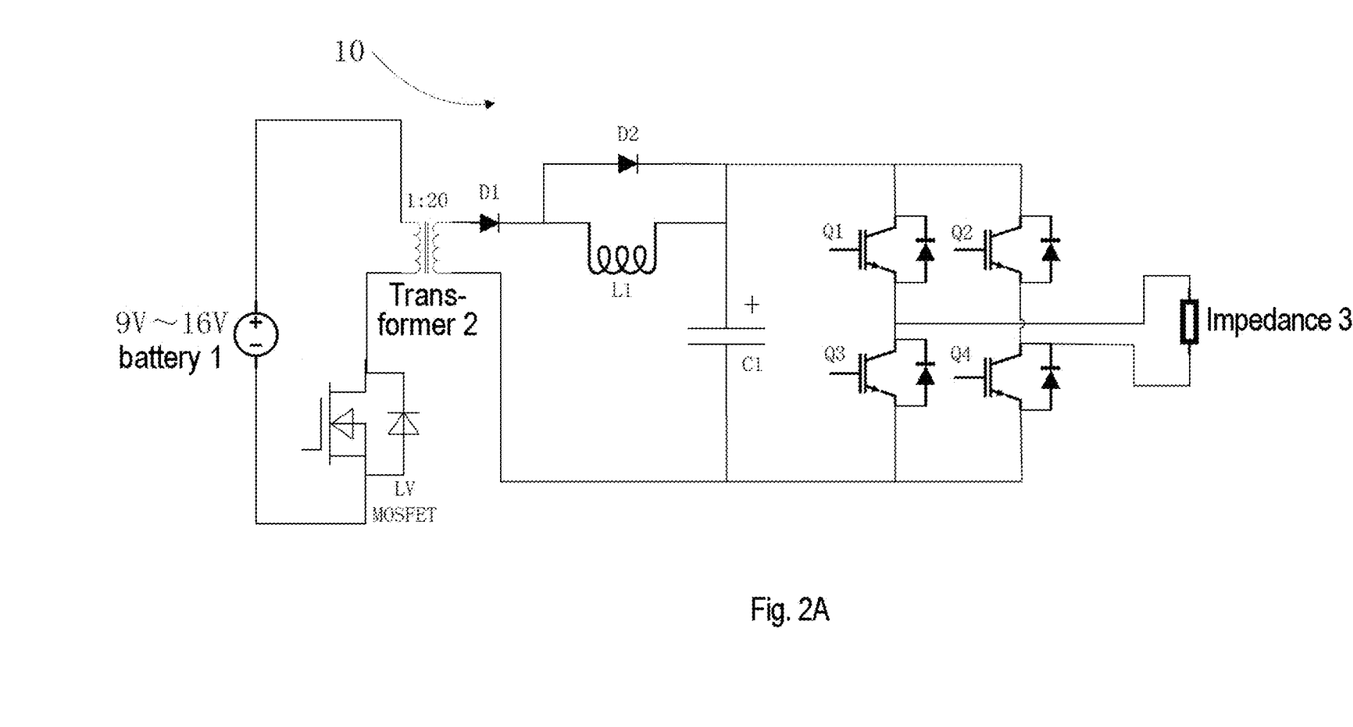
FIG. 2A is a detailed circuit diagram of the power circuit shown in FIG. 1.

FIG. 2A is a circuit diagram of the power circuit shown in FIG. 1. As shown in FIG. 2A, the power circuit 10 comprises a power source 1, for example, a 9 V-16 V battery, and a low-voltage metal oxide semiconductor field-effect transistor (MOSFET) that are coupled to the primary side winding of a transformer 2 with a turns ratio of 1:20, and a charging branch and a discharging branch that are coupled to the secondary side winding of the transformer 2. The charging branch comprises diodes D1 and D2, an inductor L1, and a capacitor C1, while the discharging branch is a full-bridge comprising four transistors Q1, Q2, Q3, and Q4. An impedance 3, for example, a human body, is connected between the bridge arm comprising transistors Q1 and Q3 and the collector of transistor Q4.

Figure 2B:
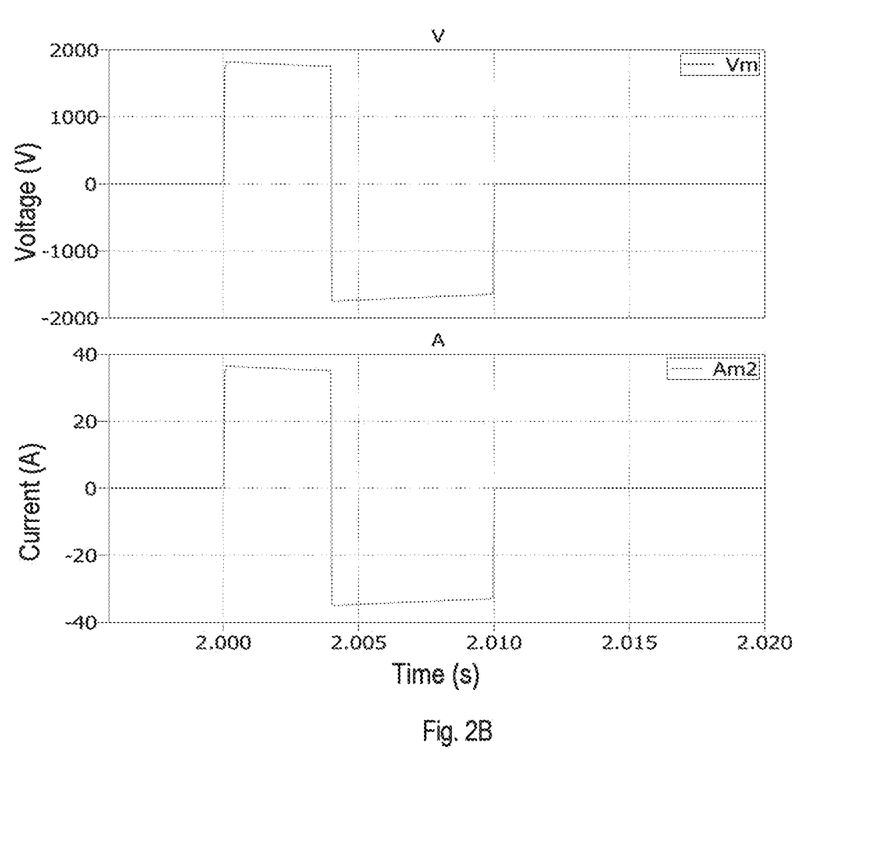
FIG. 2B shows waveforms of currents and voltages output by the power circuit shown in FIG. 2A.

FIG. 2B shows the waveforms of voltages and currents output by the power circuit shown in FIG. 2A. As shown in FIG. 2B, when the impedance offered by the human body was 50 ohms, the peak value of the output current reached about 40 A, and the voltage applied on the capacitor C1 and the transformer 2 might be as high as 2100 V, which requires an additional isolation device. There may be few available transistors that can be used as transistor Q1, Q2, Q3, or Q4, and the available transistors may be expensive. For example, IXYS IXBF32N300, which is a 3.3 kilovolts (KV) insulated-gate bipolar transistor (IGBT), may need to be used as transistor Q1, Q2, Q3, or Q4 (e.g., there may be no other suitable 3.3 KV IGBT, other than IXYS IXBF32N300, that is available and meets the needs of an AED).

As a result, some power circuits for AEDs (e.g., power circuits shown in and/or described with respect to FIGS. 1, 2A and 2B) may have short supply cycles and long delivery cycles, and may be expensive.

Figure 3:
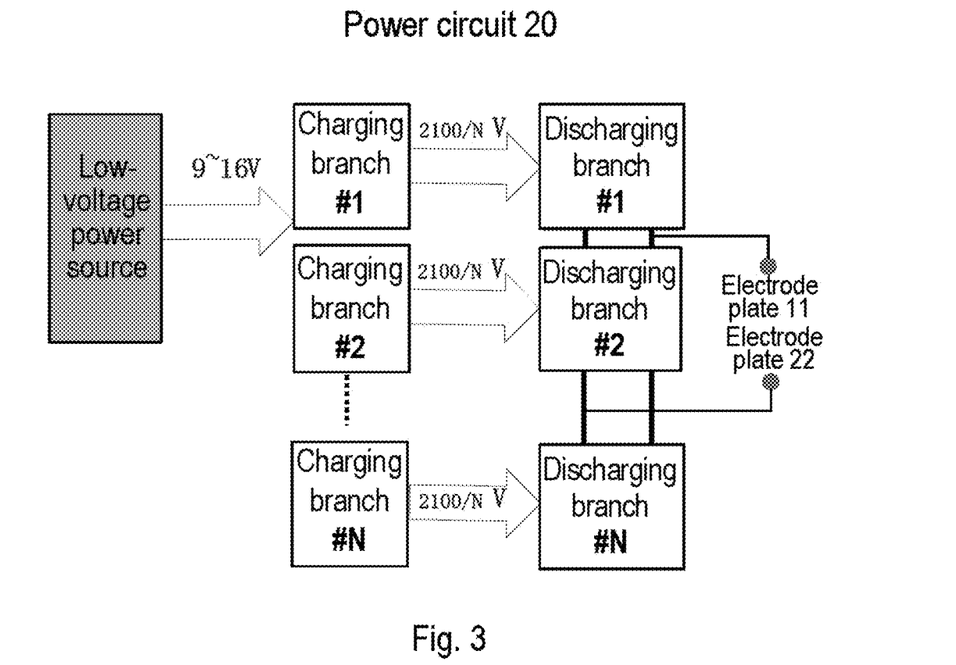
FIG. 3 is a schematic block diagram of a power circuit for an AED according to an embodiment of the present disclosure.

FIG. 3 is a block diagram of a power circuit for an AED according to an embodiment of the present disclosure. As shown in FIG. 3, the power circuit 20 comprises a 9 V-16 V low-voltage power source, charging branches #1 to #N, discharging branches #1 to #N, and electrode plates 11 and 22, where N is an integer greater than or equal to 2, and wherein N discharging branches are cascaded in sequence, and the electrode plates 11 and 22 are coupled between the first discharging branch and the Nth discharging branch. Other voltages of the low-voltage power source are within the scope of the present disclosure.

As shown in FIG. 3, each of the N charging branches converts a low voltage of 9 V-16 V into a high voltage of 2100/N V and supplies it to the corresponding discharging branch, and N discharging branches pass through the current pulses output by the electrode plates 11 and 22. Other voltages of the high voltage are within the scope of the present disclosure.

It should be understood that although FIG. 3 shows only two electrode plates 11 and 22, the present disclosure is not limited thereto, and more or less electrode plates may be provided according to actual needs.

Figure 4A:
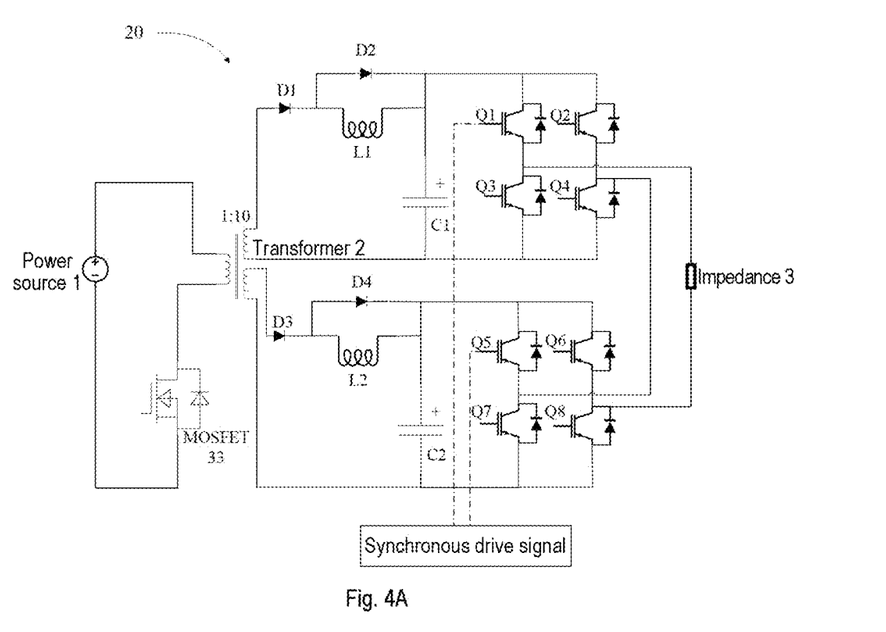
FIG. 4A is a circuit diagram of a power circuit with a two-stage cascade according to an embodiment of the present disclosure.

FIG. 4A is a circuit diagram of a power circuit with a two-stage cascade according to an embodiment of the present disclosure.

As shown in FIG. 4A, a power source 1, for example, a 9 V-16 V battery, and a low-voltage MOSFET 33 are connected in series to the primary side winding of the transformer 2. The transformer 2 comprises two secondary side windings, the first winding being coupled to the first charging and discharging branch, the second winding being coupled to the second charging and discharging branch. Since two secondary side windings are used, the turns ratio of each secondary side winding is changed from 1:20 as shown in FIG. 2A to 1:10 to convert the supply voltage of 9 V-16 V to a high voltage of 2100 V. Other quantities of the secondary side windings of the transformer 2 (e.g., more than two secondary windings of the transformer 2) are within the scope of the present disclosure.

In some examples, the first charging branch coupled to the first secondary side winding comprises diodes D1 and D2, an inductor L1, and a capacitor C1, wherein the diode D1, the inductor L1, and the capacitor C1 are connected in series to the first secondary side winding, and the diode D2 is connected across the inductor L1. The first discharging branch coupled to the first secondary side winding comprises a full bridge comprising transistors Q1, Q2, Q3, and Q4. The second charging branch coupled to the second secondary side winding comprises diodes D3 and D4, an inductor L2, and a capacitor C2, which are connected in the same manner as the first charging branch, and the second discharging branch comprises a full bridge comprising transistors Q5, Q6, Q7, and Q8.

In the embodiment shown in FIG. 4A, the collector of transistor Q4 is coupled to a bridge arm comprising transistors Q5 and Q7 to form a cascade connection, and an impedance 3, for example, a human body, is coupled between the bridge arm comprising Q1 and Q3 and the collector of transistor Q8.

Figure 4B:
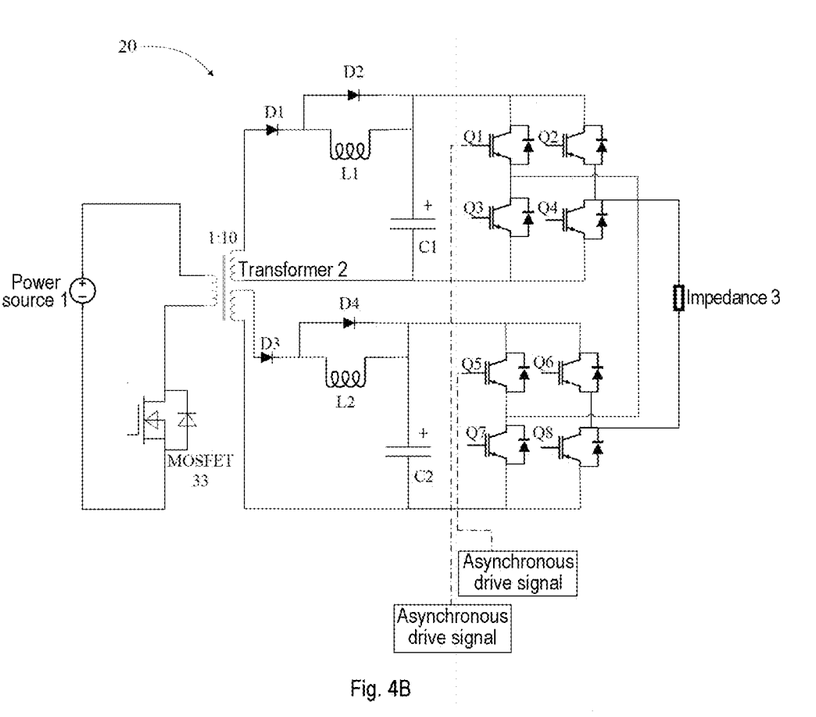
FIG. 4B is a circuit diagram of a power circuit with a two-stage cascade according to another embodiment of the present disclosure.

FIG. 4B is a circuit diagram of a power circuit with a two-stage cascade according to another embodiment of the present disclosure. The circuit shown in FIG. 4B may be substantially the same as that shown in FIG. 4A, except that the impedance 3 shown in FIG. 4B is coupled between the collector of transistor Q4 and the collector of transistor Q8, and that the arm comprising transistors Q1 and Q3 is coupled to the bridge arm comprising transistors Q5 and Q7 to form a cascade connection between the two discharging branches.

It should be noted that in the power circuit 20 shown in FIG. 4A and FIG. 4B, the drive signals for the transistors in the full bridge may be synchronous or asynchronous. FIG. 4A shows a case where the drive signals are synchronous, and FIG. 4B shows a case wherein the drive signals are asynchronous.

It should be understood that although FIG. 4A and FIG. 4B show only synchronous or asynchronous drive signals for transistors Q1 and Q5, these drive signals equally apply to transistors Q2 and Q6, transistors Q3 and Q7, and transistors Q4 and Q8.

Figure 4C:
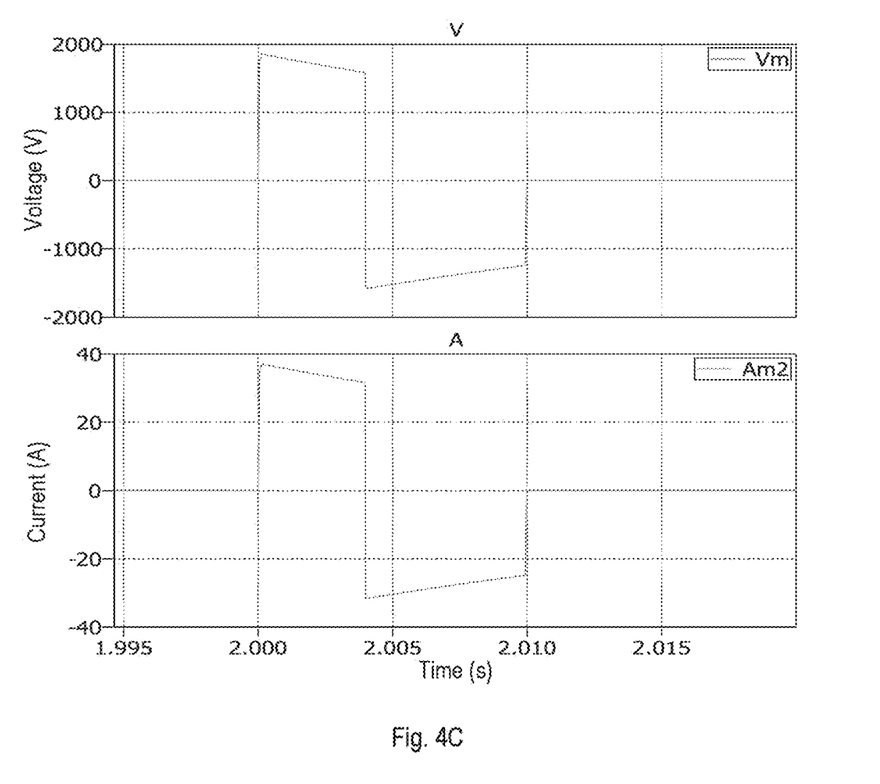
FIG. 4C shows waveforms of currents and voltages output by the power circuit shown in FIG. 4A or FIG. 4B.

FIG. 4C shows waveforms of voltages and currents output by the power circuits shown in FIG. 4A and FIG. 4B. As shown in FIG. 4C and FIG. 2B, the power circuit 20 according to an embodiment of the present disclosure can deliver substantially the same performance as the existing power circuit 10 shown in FIG. 2A, that is, generating an output voltage with a peak value of about 2000 V and an output current with a peak value of about 40 A.

In the configuration shown in FIG. 4A and FIG. 4B, the two secondary side windings of the transformer 2 and each of the capacitors C1 and C2 may only need to bear the relatively low voltage of 1050 V. In addition, for transistors Q1 to Q8, commonly used devices, such as 1.7 KV IGBTs or 2 KV SiC MOSFETs, may also be selected, without the need for a more expensive device (e.g., IXYS IXBF32N300) used in an existing power circuit, which allows a reduction in costs while increasing reliability.

It should be understood that the manner of coupling the impedance 3 shown in FIG. 4A and FIG. 4B and the manner of cascading discharging branches may be arbitrarily set between pairwise cascade connections with two or more stages.

Figure 5A:
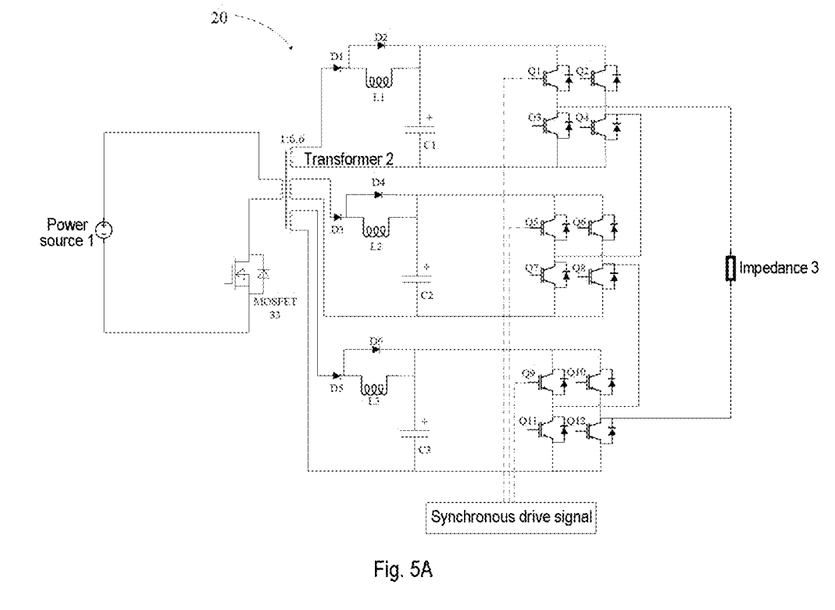
FIG. 5A is a circuit diagram of a power circuit with a three-stage cascade according to an embodiment of the present disclosure.

FIG. 5A is a circuit diagram of a power circuit 20 having a three-stage cascade according to an embodiment of the present disclosure. As shown in FIG. 5A, the transformer 2 comprises three secondary side windings, the first winding being coupled to the first charging and discharging branch, the second winding being coupled to the second charging and discharging branch, the third winding being coupled to the third charging and discharging branch. Since three secondary side windings are used, the turns ratio of each secondary side winding can be 1:6.6 to convert a supply voltage of 9 V-16 V to a high voltage of 2100 V.

The first charging branch coupled to the first secondary side winding comprises diodes D1 and D2, an inductor L1, and a capacitor C1, wherein the diode D1, the inductor L1, and the capacitor C1 are connected in series to the first secondary side winding, and the diode D2 is connected across the inductor L1. The first discharging branch coupled to the first secondary side winding is a full bridge comprising transistors Q1, Q2, Q3, and Q4; the second charging branch coupled to the second secondary side winding comprises diodes D3 and D4, an inductor L2, and a capacitor C2, which are connected in the same manner as the first charging branch, and the second discharging branch is a full bridge comprising transistors Q5, Q6, Q7, and Q8; and the third charging branch coupled to the third secondary side winding comprises diodes D5 and D6, an inductor L3, and a capacitor C3, which are connected in the same manner as the first charging branch, and the third discharging branch is a full bridge comprising transistors Q9, Q10, Q11, and Q12.

As shown in FIG. 5A, an impedance 3, for example, a human body, is coupled between the bridge arm of the first discharging branch that comprises transistors Q1 and Q3 and the collector of transistor Q12 of the third discharging branch. The collector of transistor Q4 of the full bridge of the first discharging branch is connected to the bridge arm of the full bridge of the second discharging branch that comprises transistors Q5 and Q7, and the collector of transistor Q8 of the full bridge of the second discharging branch is connected to the bridge arm of the full bridge of the third discharging branch that comprises transistors Q9 and Q11, which forms a cascade connection of three discharging branches.

In the power circuit 20 shown in FIG. 5A, the drive signals for each transistor in the full bridge may be synchronous, and the synchronous drive signals for transistors Q1, Q5 and Q9 are also applicable to transistors Q2, Q6 and Q10; transistors Q3, Q7 and Q11; and transistors Q4, Q8 and Q12.

Figure 5B:
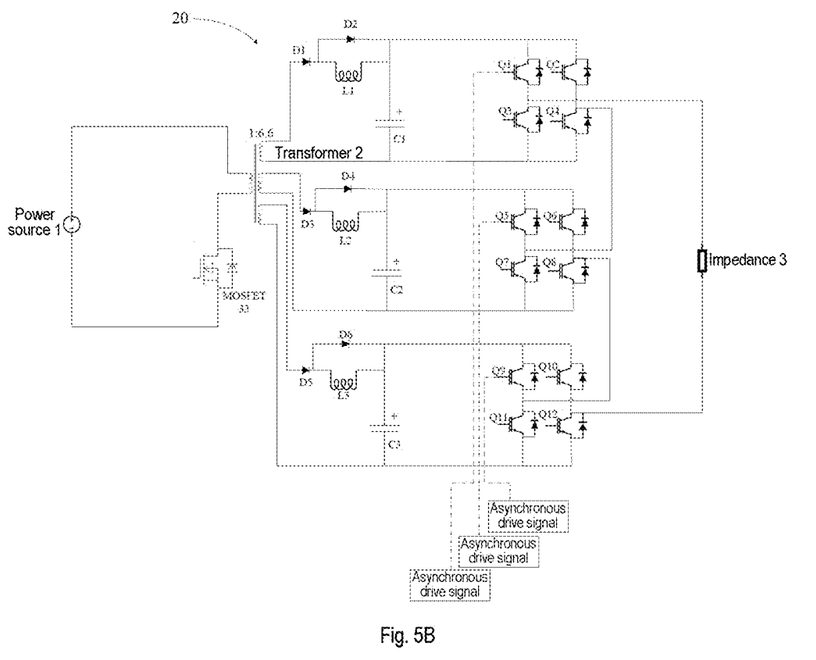
FIG. 5B is a circuit diagram of a power circuit with a three-stage cascade according to another embodiment of the present disclosure.

The driving signals of the transistors in the full bridge in the power circuit 20 shown in FIG. 5A may also be asynchronous, which is the case shown in FIG. 5B. Likewise, the asynchronous drive signals for transistors Q1, Q5 and Q9 also apply to transistors Q2, Q6 and Q10; transistors Q3, Q7 and Q11; and transistors Q4, Q8 and Q12.

It should be understood that the manner of coupling the impedance 3 shown in FIG. 5A and FIG. 5B and the manner of cascading three discharging branches may also be set as shown in FIG. 4B. For example, the impedance 3 is coupled between the collector of transistor Q4 and the collector of transistor Q12, the bridge arm comprising transistors Q1 and Q3 is connected to the bridge arm comprising transistors Q5 and Q7, and the collector of transistor Q8 is connected to the bridge arm comprising transistors 9 and Q11, which forms a cascade connection of three discharging branches.

It should also be understood that the above-described manner of coupling the impedance 3 and manner of cascading discharging branches are only exemplary, rather than limiting the present disclosure, and may be arbitrarily set as required. When N (N is an integer greater than or equal to 2) discharging branches are used, the manner of cascading one pair of discharging branches may be the same as or different from that of cascading another pair of discharging branches.

In the configuration shown in FIG. 5A and FIG. 5B, the three secondary side windings of the transformer 2 and each of the capacitors C1, C2, and C3 may only need to bear the relatively low voltage of 700 V, which makes isolation easier. In addition, for transistors Q1 to Q12, commonly used devices, such as 1.2 KV IGBTs or 1.2 KV SiC MOSFETs, may also be selected, which allows a reduction in costs while increasing reliability.

It should be understood that the drive signals of the transistors of the full bridges shown in FIG. 4A, FIG. 4B, FIG. 5A, and FIG. 5B are provided by another controller (not shown in any drawings), and since its operating principle may be the same as that of an existing power circuit for an AED, it will not be detailed again herein.

It should be pointed out that, for illustrative purposes only, in FIG. 4A, FIG. 4B, FIG. 5A, and FIG. 5B, the electrode plates shown in FIG. 3 are replaced by connecting lines at both ends of the impedance 3.

It should also be pointed out that although transistors Q1 to Q12 are shown as insulated-gate bipolar transistors (IGBTs) in FIG. 4A, FIG. 4B, FIG. 5A, and FIG. 5B, the present disclosure is not limited thereto, and any other type of transistor (that performs the same function, for example), including, but not limited to, field-effect transistors (FETs), metal oxide semiconductor field-effect transistors (MOSFETs), junction field-effect transistors (JFETs), and dual-gate MOSFETs, may be used It should also be pointed out that the present disclosure is not limited to the circuit structure of the charging branch shown in FIG. 4A, FIG. 4B, FIG. 5A, and FIG. 5B, and that the charging branch is replaceable by any suitable circuit that can convert a low voltage to a high voltage.

At least some embodiments are defined by the examples given below.

Example 1. A power circuit for a portable device, comprising a power source (e.g., a battery-driven power source); a transformer comprising a primary winding (e.g., one primary winding) and N secondary windings, wherein N is an integer greater than or equal to 2, and wherein the primary winding is electrically coupled to the power source; N charging and discharging branches, wherein the N charging and discharging branches are respectively connected to N secondary windings and are cascaded in sequence; and a plurality of electrode plates configured to be connected to an external load, wherein electrode plates of the plurality of electrode plates are electrically coupled to one or more output nodes of the N charging and discharging branches (e.g., the electrode plates of the plurality of electrode plates are electrically coupled to one of the output nodes of the N cascaded charging and discharging branches, respectively).

Example 2. The power circuit according to example 1, wherein a charging and discharging branch of the N charging and discharging branches comprises a charging branch and a discharging branch, wherein N discharging branches of the N charging and discharging branches are cascaded with each other (e.g., each charging and discharging branch of the N charging and discharging branches may comprise a charging branch and a discharging branch). In an example, the N charging and discharging branches comprise N pairs of charging branches and discharging branches, wherein the N discharging branches in the N pairs of charging branches and discharging branches are cascaded with each other.

Example 3. The power circuit according to example 2, wherein a charging branch of the N charging and discharging branches comprises a capacitor that is charged through the charging branch during charging to increase a voltage output to a discharging branch.

Example 4. The power circuit according to example 3, wherein the charging branch comprises a first diode, an inductor, and a second diode, wherein the second diode is connected across the inductor, and wherein the first diode, the inductor, and the capacitor are connected in series.

Example 5. The power circuit according to example 4, wherein an anode of the first diode is connected to a first end of a secondary winding, wherein a cathode of the first diode is connected to a first end of the inductor, wherein an anode of the second diode is connected to the cathode of the first diode, wherein a cathode of the second diode is connected to a second end of the inductor, wherein a first end of the capacitor is connected to the second end of the inductor, and wherein a second end of the capacitor is connected to a second end of the secondary winding.

Example 6. The power circuit according to example 5, wherein the discharging branch comprises a full-bridge circuit electrically coupled across the capacitor.

Example 7. The power circuit according to example 6, the plurality of electrode plates are connected between an output node of the full-bridge circuit and an output node of a second full-bridge circuit of a second discharging branch of the N discharging branches. In an example, the full-bridge circuit may correspond to an initial full-bridge circuit of an initial discharging branch of the N discharging branches (e.g., the initial discharging branch may correspond to discharging branch #1 in FIG. 3). In an example, the second full-bridge circuit may correspond to a last full-bridge circuit of a last discharging branch of the N discharging branches (e.g., the last discharging branch may correspond to an Nth discharging branch of the N discharging branches, such as discharging branch #N in FIG. 3).

Example 8. The power circuit according to example 6, wherein the full-bridge circuit comprises a first output node and a second output node, wherein a second full-bridge circuit, of a second discharging branch of the N discharging branches, comprises a third output node and a fourth output node, wherein the first output node of the full-bridge circuit is connected to the third output node of the second full-bridge circuit, wherein the fourth output node of the second full-bridge circuit is connected to an output node of a third full-bridge circuit of a third discharging branch of the N discharging branches, and wherein the external load is electrically coupled between the second output node of the full-bridge circuit and a fifth output node of a fourth full-bridge circuit of a fourth discharging branch of the N discharging branches. In an example, the full-bridge circuit may correspond to an initial full-bridge circuit of an initial discharging branch of the N discharging branches (e.g., the initial discharging branch may correspond to discharging branch #1 in FIG. 3). In an example, the fourth full-bridge circuit may correspond to a last full-bridge circuit of a last discharging branch of the N discharging branches (e.g., the last discharging branch may correspond to an Nth discharging branch of the N discharging branches, such as discharging branch #N in FIG. 3).

Example 9. The power circuit according to example 8, wherein the fourth full-bridge circuit comprises a sixth output node, and wherein the plurality of electrode plates are connected between an output node, of the first output node and the second output node, of the full-bridge circuit, and an output node, of the fifth output node and the sixth output node, of the fourth full-bridge circuit.

Example 10. The power circuit according to any of examples 8 to 9, wherein the full-bridge circuit comprises a first transistor, a second transistor, a third transistor, and a fourth transistor, wherein the first output node of the full-bridge circuit is a node located on a bridge arm comprising the first transistor and the second transistor, and the second output node of the full-bridge circuit is a node located on a bridge arm comprising the third transistor and the fourth transistor.

Example 11. The power circuit according to example 2, wherein each charging branch comprises a capacitor that is charged through the charging branch during charging to increase the voltage output to the corresponding discharging branch.

Example 12. The power circuit according to example 11, wherein each charging branch further comprises a first diode, an inductor, and a second diode wherein the second diode is connected across the inductor, and wherein the first diode, the inductor, and the capacitor are connected in series.

Example 13. The power circuit according to example 12, wherein the anode of the first diode is connected to one end of the corresponding secondary winding and the cathode thereof is connected to one end of the inductor, the anode of the second diode is connected to the cathode of the first diode and the cathode thereof is connected to the other end of the inductor, and one end of the capacitor is connected to the other end of the inductor and the other end thereof is connected to the other end of the corresponding secondary winding.

Example 14. The power circuit according to example 13, wherein each discharging branch comprises a full-bridge circuit electrically coupled across the capacitor.

Example 15. The power circuit according to example 14, wherein the plurality of electrode plates are connected between an output node of a first full-bridge circuit (e.g., an initial full-bridge circuit among N full-bridge circuits) and an output node of a last full-bridge circuit among the N full-bridge circuits (e.g., an Nth full-bridge circuit among the N full-bridge circuits).

Example 16. The power circuit according to example 15, wherein each of the N full-bridge circuits comprises a first output node and a second output node, one of the first output node and the second output node of the first full-bridge circuit is connected to one of the first output node and the second output node of the second full-bridge circuit, the other of the first output node and the second output node of the second full-bridge circuit is connected to one of the first output node and the second output node of the third full-bridge circuit, and so on until the Nth full-bridge circuit, and the external load is electrically coupled between the other of the first output node and the second output node of the first full-bridge circuit and the other of the first output node and the second output node of the Nth full-bridge circuit.

Example 17. The power circuit according to example 16, wherein each full-bridge circuit comprises a first transistor, a second transistor, a third transistor, and a fourth transistor, wherein the first output node of each full-bridge circuit is a node located on the bridge arm comprising the first transistor and the third transistor, and the second output node of each full-bridge circuit is a node located on the bridge arm comprising the second transistor and the fourth transistor.

Example 18. The power circuit according to any of examples 6 to 10 and/or 14 to 17, wherein respective drive signals for the N full-bridge circuits of the N discharging branches are synchronous.

Example 19. The power circuit according to any of examples 6 to 10 and/or 14 to 17, wherein respective drive signals for the N full-bridge circuits of the N discharging branches are asynchronous.

Example 20. The power circuit according to any of examples 1 to 19, wherein a number of turns of a secondary winding of the N secondary windings is a function of N (such as where the number of turns decreases as N increases).

Example 21. An automated external defibrillator comprising the power circuit according to any of examples 1 to 20.

While the present disclosure has been disclosed above with a description of specific embodiments of the present disclosure, it should be understood that those of ordinary skill in the art can design various modifications, improvements, or equivalents thereof to the present disclosure without departing from the spirit and scope of the appended claims. Such modifications, improvements, or equivalents thereof should also be deemed to fall within the scope of protection of the present disclosure.

The invention claimed is:

1. A power circuit for a portable device, wherein the power circuit comprises:
 a battery-driven power source;
 a transformer comprising a primary winding and N secondary windings, wherein N is an integer greater than or equal to 2, and wherein the primary winding is electrically coupled to the battery-driven power source;
 N charging and discharging branches, wherein the N charging and discharging branches are respectively connected to the N secondary windings and are cascaded in sequence; and
 a plurality of electrode plates configured to be connected to an external load, wherein electrode plates of the plurality of electrode plates are electrically coupled to one or more output nodes of the N charging and discharging branches.

2. The power circuit of claim 1, wherein a charging and discharging branch of the N charging and discharging branches comprises a charging branch and a discharging branch, and wherein N discharging branches of the N charging and discharging branches are cascaded with each other.

3. The power circuit of claim 1, wherein a charging branch of the N charging and discharging branches comprises a capacitor that is charged through the charging branch during charging to increase a voltage output to a discharging branch.

4. The power circuit of claim 3, wherein the charging branch comprises a first diode, an inductor, and a second diode, wherein the second diode is connected across the inductor, and wherein the first diode, the inductor, and the capacitor are connected in series.

5. The power circuit of claim 4, wherein an anode of the first diode is connected to a first end of a secondary winding, wherein a cathode of the first diode is connected to a first end of the inductor, wherein an anode of the second diode is connected to the cathode of the first diode, wherein a cathode of the second diode is connected to a second end of the inductor, wherein a first end of the capacitor is connected to the second end of the inductor, and wherein a second end of the capacitor is connected to a second end of the secondary winding.

6. The power circuit of claim 5, wherein the discharging branch comprises a full-bridge circuit electrically coupled across the capacitor.

7. The power circuit of claim 6, wherein the plurality of electrode plates are connected between an output node of the full-bridge circuit and an output node of a second full-bridge circuit of a second discharging branch of the N discharging branches.

8. The power circuit of claim 6, wherein:
the full-bridge circuit comprises a first output node and a second output node;
a second full-bridge circuit, of a second discharging branch of the N discharging branches, comprises a third output node and a fourth output node;
the first output node of the full-bridge circuit is connected to the third output node of the second full-bridge circuit;
the fourth output node of the second full-bridge circuit is connected to an output node of a third full-bridge circuit of a third discharging branch of the N discharging branches; and
the external load is electrically coupled between the second output node of the full-bridge circuit and a fifth output node of a fourth full-bridge circuit of a fourth discharging branch of the N discharging branches.

9. The power circuit of claim 8, wherein the fourth full-bridge circuit comprises a sixth output node, and wherein the plurality of electrode plates are connected between:
an output node, of the first output node and the second output node, of the full-bridge circuit; and
an output node, of the fifth output node and the sixth output node, of the fourth full-bridge circuit.

10. The power circuit of claim 8, wherein the full-bridge circuit comprises a first transistor, a second transistor, a third transistor, and a fourth transistor, wherein the first output node of the full-bridge circuit is a node located on a bridge arm comprising the first transistor and the second transistor, and wherein the second output node of the full-bridge circuit is a node located on a bridge arm comprising the third transistor and the fourth transistor.

11. The power circuit of claim 6, wherein respective drive signals for one or more full-bridge circuits of the N discharging branches are synchronous.

12. The power circuit of claim 6, wherein respective drive signals for one or more full-bridge circuits of the N discharging branches are asynchronous.

13. The power circuit of claim 1, wherein a first discharging branch of the N charging and discharging branches comprises a first set of two or more transistors, wherein a second discharging branch of the N charging and discharging branches comprises a second set of two or more transistors.

14. An automated external defibrillator, comprising:
a power circuit comprising:
a battery-driven power source;
a transformer comprising a primary winding and N secondary windings, wherein N is an integer greater than or equal to 2, and wherein the primary winding is electrically coupled to the battery-driven power source;
N charging and discharging branches, wherein the N charging and discharging branches are respectively connected to the N secondary windings and are cascaded in sequence, wherein a first charging branch of the N charging and discharging branches comprises a first capacitor, a first diode, a first inductor, and a second diode, wherein a second charging branch of the N charging and discharging branches comprises a second capacitor, a third diode, a second inductor, and a fourth diode; and
a plurality of electrode plates configured to be connected to an external load, wherein electrode plates of the plurality of electrode plates are electrically coupled to one or more output nodes of the N charging and discharging branches.

15. The automated external defibrillator of claim 14, wherein N discharging branches of the N charging and discharging branches are cascaded with each other.

16. The automated external defibrillator of claim 14, wherein the first capacitor is charged through the first charging branch during charging to increase a voltage output to a first discharging branch.

17. The automated external defibrillator of claim 16, wherein the second diode is connected across the first inductor, and wherein the first diode, the first inductor, and the first capacitor are connected in series.

18. The automated external defibrillator of claim 17, wherein an anode of the first diode is connected to a first end of a corresponding secondary winding, wherein a cathode of the first diode is connected to a first end of the first inductor, wherein an anode of the second diode is connected to the cathode of the first diode, wherein a cathode of the second diode is connected to a second end of the first inductor, wherein a first end of the first capacitor is connected to the second end of the first inductor, and wherein a second end of the first capacitor is connected to a second end of the corresponding secondary winding.

19. The automated external defibrillator of claim 18, wherein the discharging branch comprises a full-bridge circuit electrically coupled across the first capacitor.

20. A power circuit comprising:
a power source;
a transformer comprising a primary winding and N secondary windings, wherein N is an integer greater than or equal to 2, and wherein the primary winding is electrically coupled to the power source;
N charging and discharging branches, wherein the N charging and discharging branches are respectively connected to the N secondary windings and are cascaded in sequence, wherein a charging branch of the N charging and discharging branches comprises a capacitor, a first diode, an inductor, and a second diode; and
a plurality of electrode plates configured to be connected to an external load, wherein electrode plates of the plurality of electrode plates are electrically coupled to one or more output nodes of the N charging and discharging branches.

\* \* \* \* \*